US012678391B2

(12) United States Patent　　(10) Patent No.:　US 12,678,391 B2
　　Enomoto et al.　　　　　　　　(45) Date of Patent:　　Jul. 14, 2026

(54) WATER-IN-OIL EMULSION SUNSCREEN COSMETIC

(71) Applicant: Shiseido Company, Ltd., Tokyo (JP)

(72) Inventors: Ayumu Enomoto, Tokyo (JP); Keita Nishida, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 915 days.

(21) Appl. No.: 17/770,482

(22) PCT Filed: Oct. 13, 2020

(86) PCT No.: PCT/JP2020/038568
　　§ 371 (c)(1),
　　(2) Date: Apr. 20, 2022

(87) PCT Pub. No.: WO2021/079783
　　PCT Pub. Date: Apr. 29, 2021

(65) Prior Publication Data
　　US 2022/0395445 A1　　Dec. 15, 2022

(30) Foreign Application Priority Data

Oct. 23, 2019　(JP) ................................. 2019-192750

(51) Int. Cl.
| | |
|---|---|
| *A61K 8/60* | (2006.01) |
| *A61K 8/27* | (2006.01) |
| *A61K 8/368* | (2006.01) |
| *A61K 8/44* | (2006.01) |
| *A61K 8/67* | (2006.01) |
| *A61Q 17/04* | (2006.01) |

(52) U.S. Cl.
　　CPC ............... *A61K 8/676* (2013.01); *A61K 8/27* (2013.01); *A61K 8/368* (2013.01); *A61K 8/44* (2013.01); *A61K 8/602* (2013.01); *A61K 8/675* (2013.01); *A61Q 17/04* (2013.01)

(58) Field of Classification Search
　　None
　　See application file for complete search history.

(56) References Cited

FOREIGN PATENT DOCUMENTS

| | | | | |
|---|---|---|---|---|
| JP | 2013173728 | * | 9/2013 | |
| JP | 2013173728 A | * | 9/2013 | |
| JP | 2015-124203 A | | 7/2015 | |
| JP | 2017-178887 A | | 10/2017 | |
| JP | 2018100250 A | * | 6/2018 | |
| WO | WO-0015180 A1 | * | 3/2000 | ............... C11D 7/24 |

OTHER PUBLICATIONS

Mintel GNPD, "Waterproof Sunblock," Tanning Research Laboratories, Hawaiian Tropic Splash Kids SPF 45, ID 10167366, 2004, 3 pages.

* cited by examiner

*Primary Examiner* — Celeste A Roney
(74) *Attorney, Agent, or Firm* — Foley & Lardner LLP

(57) ABSTRACT

[Problem] An objective of the present invention is to provide a water-in-oil emulsion sunscreen cosmetic that allows a medicinal agent to be blended into the internal phase, while having high ultraviolet protection power. [Solution] The sunscreen cosmetic of the present invention is characterized by comprising: (A) an ultraviolet absorbing agent; (B) a medicinal agent selected from the group consisting of L-ascorbic acid and derivatives thereof, tranexamic acid and derivatives thereof, alkoxysalicylic acid and derivatives thereof, glycyrrhizinic acid and derivatives thereof, and nicotinic acid and derivatives thereof; (C) a water-soluble thickener that is not sugar-derived; and (D) water.

4 Claims, No Drawings

WATER-IN-OIL EMULSION SUNSCREEN COSMETIC

CROSS-REFERENCE TO RELATED APPLICATIONS

This application is the U.S. National Stage of PCT/JP2020/038568, filed Oct. 13, 2020, which claims priority to JP 2019-192750, filed Oct. 23, 2019.

TECHNICAL FIELD

The present invention relates to a water-in-oil emulsion sunscreen cosmetic that allows a medicinal agent to be blended into the internal phase, while having high ultraviolet protection power.

BACKGROUND ART

Ultraviolet rays are one of the factors causing damage to skin, and exposure to strong ultraviolet rays is known to result in excessive generation of melanin pigments and to be a cause of spots and freckles. Thus, protecting skin from harm due to ultraviolet rays and allowing skin that has been damaged by ultraviolet rays to recover is one important problem to be addressed in skin care and body care.

As cosmetics for protecting skin from harm caused by ultraviolet rays, there are sunscreen cosmetics that suppress the amount of ultraviolet rays reaching the skin by absorbing or scattering UBA and UVB. Among sunscreen cosmetics, water-in-oil emulsion cosmetics are favored for being able to stably blend ultraviolet absorbing agents or ultraviolet scattering agents in order to obtain high ultraviolet protection power, and being able to obtain sufficient water resistance. However, in water-in-oil emulsions, the external phase is the oil phase. Thus, there is a need to suppress oiliness and stickiness.

For example, Patent Document 1 describes a water-in-oil emulsion sunscreen cosmetic in which a silicone backbone powder, a polymethyl methacrylate power and a hydrophobically treated flake-shaped powder are combined and blended, thereby resulting in a cosmetic that provides high ultraviolet protection effects and that has no oiliness or stickiness.

On the other hand, as cosmetics for allowing the skin to recover from damage due to ultraviolet rays, skin-care cosmetics blending with medicinal agents such as whiteners and anti-inflammatory agents are favored.

Until now, a water-in-oil emulsion cosmetic that provides medicinal effects and that increases ultraviolet protection power has not been considered.

RELATED ART

Patent Documents

Patent Document 1: JP 2013-63954 A

SUMMARY OF THE INVENTION

Problem to be Solved by the Invention

An objective of the present invention is to provide a water-in-oil emulsion sunscreen cosmetic that provides medicinal effects while also having sufficient ultraviolet protection power.

Means for Solving the Problem

As a result of performing diligent investigations towards solving the aforementioned problem, the inventors discovered that the ultraviolet protection power of an ultraviolet absorbing agent increases when a certain type of water-soluble thickener and a specific medicinal component are combined and blended, thereby completing the present invention.

In other words, the present invention provides a water-in-oil emulsion sunscreen cosmetic comprising:
- (A) an ultraviolet absorbing agent;
- (B) a medicinal agent selected from the group consisting of L-ascorbic acid and derivatives thereof, tranexamic acid and derivatives thereof, alkoxysalicylic acid and derivatives thereof, glycyrrhizinic acid and derivatives thereof, and nicotinic acid and derivatives thereof;
- (C) a water-soluble thickener that is not sugar-derived; and
- (D) water.

Effects of the Invention

The cosmetic of the present invention, by having the above-mentioned features, can increase the ultraviolet protection power of an ultraviolet absorbing agent blended into the sunscreen cosmetic. Additionally, by combining a water-in-oil emulsion with a specific water-soluble thickener, a sunscreen cosmetic having a watery feeling in use like that of an oil-in-water emulsion, while being provided with water resistance, can be realized.

MODES FOR CARRYING OUT THE INVENTION

The sunscreen cosmetic of the present invention is characterized by comprising: (A) an ultraviolet absorbing agent; (B) a medicinal agent selected from the group consisting of L-ascorbic acid and derivatives thereof, tranexamic acid and derivatives thereof, alkoxysalicylic acid and derivatives thereof, glycyrrhizinic acid and derivatives thereof, and nicotinic acid and derivatives thereof; (C) a water-soluble thickener that is not sugar-derived; and (D) water. Hereinafter, the components constituting the cosmetic of the present invention will be explained in detail.

<(A) Ultraviolet Absorbing Agent>

As the (A) ultraviolet absorbing agent (hereinafter sometimes referred to simply as "Component (A)") blended in the sunscreen cosmetic of the present invention, one that is normally blended into sunscreen cosmetics may be used. Examples include benzoic acid derivatives, salicylic acid derivatives, cinnamic acid derivatives, dibenzoyl methane derivatives, ββ-diphenyl acrylate derivatives, benzophenone derivatives, benzylidene camphor derivatives, phenylbenzimidazole derivatives, triazine derivatives, phenylbenzotriazole derivatives, anthranil derivatives, imidazoline derivatives, benzalmalonate derivatives, 4,4-diaryl butadiene derivatives and the like. Hereinafter, specific examples and product names will be mentioned, but there is no limitation thereto.

Examples of benzoic acid derivatives include ethyl para-aminobenzoate (PABA), ethyl-dihydroxypropyl PABA, ethylhexyl-dimethyl PABA (e.g., "Escalol 507"; ISP), glyceryl PABA, PEG-25-PABA (e.g., "Uvinul P25"; BASF), diethylamino hydroxybenzoyl hexyl benzoate (e.g., "Uvinul A Plus") and the like.

Examples of salicylic acid derivatives include homosalate ("Eusolex HMS"; Rona/EM Industries), ethylhexyl salicylate or octyl salicylate (e.g., "Neo Heliopan OS"; Haarmann & Reimer), dipropylene glycol salicylate (e.g., "Dipsal"; Scher), TEA salicylate (e.g., "Neo Heliopan TS"; Haarmann & Reimer) and the like.

Examples of cinnamic acid derivatives include octyl methoxycinnamate or ethylhexyl methoxycinnamate (e.g., "Parsol MCX"; Hoffmann-La Roche), isopropyl methoxycinnamate, isoamyl methoxycinnamate (e.g., "Neo Heliopan E1000"; Haarmaan & Reimer), cinnoxate, DEA methoxycinnamate, diisopropyl methyl cinnamate, glyceryl ethylhexanoate dimethoxycinnamate, di-(2-ethylhexyl)-4'-methoxybenzalmalonate and the like.

Examples of dibenzoyl methane derivatives include 4-tert-butyl-4'-methoxy dibenzoyl methane (e.g., "Parsol 1789") and the like.

Examples of ββ-diphenyl acrylate derivatives include octocrylene (e.g., "Uvinul N539T"; BASF) and the like.

Examples of benzophenone derivatives include benzophenone-1 (e.g., "Uvinul 400"; BASF), benzophenone-2 (e.g., "Uvinul D50"; BASF), benzophenone-3 or oxybenzone (e.g. "Uvinul M40"; BASF), benzophenone-4 (e.g., "Uvinul MS40"; BASF), benzophenone-5, benzophenone-6 (e.g., "Helisorb 11"; Norquay), benzophenone-8 (e.g., "Spectra-Sorb UV-24"; American Cyanamid), benzophenone-9 (e.g., "Uvinul DS-49"; BASF), benzophenone-12 and the like.

Examples of benzylidene camphor derivatives include 3-benzylidene camphor (e.g., "Mexoryl SD"; Chimex), 4-methylbenzylidene camphor, benzylidene camphor sulfonic acid (e.g., "Mexoryl SL"; Chimex), camphor benzalkonium methosulfate (e.g., "Mexoryl SO"; Chimex), terephthalylidene dicamphor sulfonic acid (e.g., "Mexoryl SX"; Chimex), polyacrylamide methylbenzylidene camphor (e.g., "Mexoryl SW"; Chimex) and the like.

Examples of phenylbenzimidazole derivatives include phenylbenzimidazole sulfonic acid (e.g., "Eusolex 232"; Merck), disodium phenyldibenzimidazole tetrasulfonate (e.g., "Neo Heliopan AP"; Haarmann & Reimer) and the like.

Examples of triazine derivatives include bis-ethylhexyloxyphenol methoxyphenyl triazine (e.g., "Tinosorb S"; Ciba Specialty Chemicals), ethylhexyl triazone (e.g., "Uvinul T150"; BASF), diethylhexyl butamido triazone (e.g., "Uvasorb HEB"; Sigma 3V), 2,4,6-tris(diisobutyl-4'-aminobenzalmalonate)-s-triazine, 2,4,6-tris[4-(2-ethylhexyloxycarbonyl)anilino]-1,3,5-triazine and the like.

Examples of phenylbenzotriazole derivatives include drometrizole trisiloxane (e.g., "Silatrizole"; Rhodia Chimie), methylene bis(benzotriazolyl tetramethylbutyl phenol) (e.g., "Tinosorb M" (Ciba Specialty Chemicals)) and the like.

Examples of anthranil derivatives include menthyl anthranilate (e.g., "Neo Heliopan MA"; Haarmann & Reimer) and the like.

Examples of imidazoline derivatives include ethylhexyl dimethoxybenzylidene dioxoimidazoline propionate and the like.

Examples of benzalmalonate derivatives include polyorganosiloxanes having benzalmalonate functional groups (e.g., Polysilicone-15; "Parsol SLX"; DSM Nutrition Japan) and the like.

Examples of 4,4-diarylbutadiene derivatives include 1,1-dicarboxy (2,2'-dimethylpropyl)-4,4-diphenylbutadiene and the like.

The (A) ultraviolet absorbing agent used in the present invention may be blended as a single type or as a combination of two or more types.

The blended amount of the (A) ultraviolet absorbing agent is 3% to 40% by mass, preferably 3% to 30% by mass, and even more preferably 3% to 20% by mass relative to the entire sunscreen cosmetic. If the blended amount of the (A) ultraviolet absorbing agent is less than 3% by mass, then sufficient ultraviolet protection effects are difficult to obtain, and even if more than 40% by mass is blended, an increase in ultraviolet protection effects commensurate with the blended amount cannot be expected, and the stability and texture become worse.

<(B) Medicinal Agent>

The (B) medicinal agent (hereinafter sometimes referred to simply as "component (B)") blended into the sunscreen cosmetic of the present invention is a medicinal agent that is normally blended into cosmetics as a whitener, an anti-inflammatory agent, an anti-wrinkle agent or the like, and is selected from among L-ascorbic acid and derivatives thereof, tranexamic acid and derivatives thereof, alkoxysalicylic acid and derivatives thereof, glycyrrhizinic acid and derivatives thereof, and nicotinic acid and derivatives thereof. The respective components will be described in detail below.

L-ascorbic acid derivatives include L-ascorbic acid monoalkyl esters such as L-ascorbic acid monostearate, L-ascorbic acid monopalmitate and L-ascorbic acid monooleate; L-ascorbic acid monoesters such as L-ascorbic acid monophosphoric acid ester and L-ascorbic acid-2-sulfuric acid ester; L-ascorbic acid dialkyl esters such as L-ascorbic acid distearate, L-ascorbic acid dipalmitate and L-ascorbic acid dioleate; L-ascorbic acid trialkyl esters such as L-ascorbic acid tristearate, L-ascorbic aid tripalmitate and L-ascorbic acid trioleate; L-ascorbic acid triesters such as L-ascorbic acid triphosphoric acid ester; and L-ascorbic acid glucosides such as L-ascorbic acid 2-glucoside. In the present invention, L-ascorbic acid, L-ascorbic acid phosphoric acid ester, L-ascorbic acid-2-sulfuric acid ester, L-ascorbic acid 2-glucoside and salts thereof are preferably used.

Tranexamic acid derivatives include tranexamic acid dimers (e.g., trans-4-(trans-aminomethylcyclohexanecarbonyl)aminomethylcyclohexanecarboxylic acid hydrochloride, etc.), esters of tranexamic acid and hydroquinone (e.g., 4-(trans-aminomethylcyclohexane-carboxylic acid 4'-hydroxyphenyl ester, etc.), esters of tranexamic acid and gentisic acid (e.g., 2-(trans-4-aminomethylcyclohexylcarbonyloxy)-5-hydroxybenzoic acid, etc.), tranexamic acid amides (e.g., trans-4-aminomethylcyclohexanecarbocylic acid methylamide, trans-4-(p-methoxybenzoyl)aminomethylcyclohexanecarboxylic acid, trans-4-guanidinomethylcyclohexanecarboxylic acid, etc.) and the like. In the present invention, tranexamic acid and salts thereof are preferably used.

The alkoxysalicylic acid is salicylic acid with the hydrogen atom at one of the 3-position, the 4-position or the 5-position substituted by an alkoxy group, wherein the alkoxy group that is the substituent group is preferably one of a methoxy group, an ethoxy group, a propoxy group, an isopropoxy group, a butoxy group and an isobutoxy group, and more preferably a methoxy group or an ethoxy group. Examples of specific compounds include 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, 5-propoxysalicylic acid and the like. In the present invention, methoxysalicylic acid and salts thereof (potassium methoxysalicylate) are preferably used.

Derivatives of glycyrrhizinic acid include glycyrrhizinic acid salts, esters of glycyrrhizinic acid with higher alcohols, and the like. In the present invention, glycyrrhizinic acid and salts thereof (such as dipotassium glycyrrhizinate and mono-ammonium glycyrrhizinate) are preferably used.

The salts of the above-mentioned medicinal agents are not particularly limited. Examples include alkali metal salts or alkaline earth metal salts such as sodium salts, potassium salts and calcium salts, as well as salts such as ammonium salts and amino acid salts.

Nicotinic acid and derivatives thereof include nicotinic acid, benzyl nicotinate, nicotinic acid amide, dl-α-tocopherol nicotinate and the like. In the present invention, nicotinic acid amide is preferably used.

In the cosmetic of the present invention, the above-mentioned medicinal agents may be blended as a single type or as a combination of two or more types.

Additionally, it was observed that the rate of increase in the ultraviolet protection power tended to be even better when a medicinal agent that is not a salt is used. Thus, in the present invention, it is more preferable for the medicinal agent that is used to not be a salt.

The blended amount of the (B) medicinal agent is 0.05% to 3% by mass, preferably 0.1% to 3% by mass, and even more preferably 0.5% to 2% by mass relative to the entire sunscreen cosmetic. If the blended amount of the (B) medicinal agent is less than 0.05% by mass, then sufficient medicinal effects are difficult to obtain, and if more than 3% by mass is blended, the stability and texture become worse.

<C> Water-Soluble Thickener>

The (C) water-soluble thickener (hereinafter sometimes referred to simply as "component (C)") blended into the sunscreen cosmetic of the present invention is a water-soluble thickener that is normally blended into cosmetics, and is selected from among water-soluble thickeners excluding water-soluble thickeners that are derived from sugars. Specifically, it should preferably be selected from, without being limited to, vinyl-based polymers, acrylic-based polymers, acrylate-based synthetic polymers and hydrophobically modified polyether urethanes.

Examples of vinyl-based polymers include polyvinyl alcohol, polyvinyl acetate, polyvinyl methyl ethers, polyvinyl pyrrolidone, copolymers of vinyl pyrrolidone and vinyl acetate copolymer, carboxyvinyl polymer and the like.

Acrylic-based polymers include sodium polyacrylate, polyethyl acrylate, alkanolamine polyacrylate, copolymers of alkyl methacrylate and dimethylaminoethyl methacrylate, poly-2-acrylamido-2-methylpropane sulfonic acid, polymethacryloyloxy trimethyl ammonium, (ammonium acryloyldimethyl taurate/VP) copolymer, (dimethylacrylamide/sodium acryloyldimethyl taurate) crosspolymer ("SU-GEL"; Toho Chemical Industry) and the like.

As the acrylate-based synthetic polymer, (acrylates/steareth-20 methacrylate) copolymer (product name "Aculyn (registered trademark) 22"; Dow Chemical), (acrylates/C10-30 alkyl acrylate) crosspolymer ("Pemulen (registered trademark) TR-2", Nikko Chemicals) and the like can be used.

Hydrophobically modified polyether urethanes refer associative thickeners represented by the general formula (1) below.

$$R^1\text{-}\{(O\text{---}R^2)_k\text{---}OCONH\text{---}R^3[\text{---}NHCOO\text{---}(R^4\text{---}O)_n\text{---}R^5]_h\}_m \quad \text{Formula (1)}$$

[In the formula, $R^1$, $R^2$ and $R^4$ represent hydrocarbon groups that may be the same as or different from each other, $R^3$ represents a hydrocarbon group that may have a urethane bond, $R^5$ represents a linear or branched divalent hydrocarbon group, m is an integer greater than or equal to 2, h is an integer greater than or equal to 1, and k and n are, independent of each other, integers within the range 0 to 1000.]

A specific example of a hydrophobically modified polyether urethane is polyethylene glycol-decyl tetradeceth-hexamethylene diisocyanate copolymer. Particularly preferably examples include (PEG-240/decyl tetradeceth-20/hexamethyl diisocyanate) copolymer ("Adekanol GT-700"; Adeka Corp.) and the like.

The (C) water-soluble thickener used in the present invention may be blended as a single type or as a combination of two or more types.

The blended amount of the (C) water-soluble thickener is 0.01% to 2% by mass, preferably 0.02% to 1% by mass, 0.03% to 1% by mass, 0.05% to 1% by mass, and even more preferably 0.03% to 0.3% by mass or 0.1% to 0.3% by mass relative to the entire sunscreen cosmetic. If the blended amount is less than 0.01% by mass, then the thickening is not sufficient and the stability of the internal phase becomes poor. Additionally, if the blended amount exceeds 2% by mass, then the texture tends to be sticky.

<D> Water>

Although the (D) water (hereinafter sometimes referred to simply as "component (D)") blended into the sunscreen cosmetic of the present invention is not particularly limited, examples include ion-exchanged water, purified water and natural water.

The blended amount of the (D) water should be 13% to 80% by mass and preferably 15% to 70% by mass relative to the entire sunscreen cosmetic.

Conventionally, it was difficult to blend a whitener that is water-soluble into the internal phase (water phase) of a water-in-oil emulsion. In the water-in-oil emulsion cosmetic of the present invention, the water phase is thickened by the specific water-soluble thickener, thereby allowing the water phase and the oil phase to be blended at a ratio of 1:7 to 8:1, making it possible to stably blend the whitener.

<Optional Blended Components>

Aside from the components (A) to (D) mentioned above, components that are normally used in cosmetics may be blended into the sunscreen cosmetic of the present invention within a range not compromising the effects of the present invention.

For example, oil-based components, water-based components, alcohols, humectants, thickeners, surfactants, film agents, powder agents, ultraviolet scattering agents, stabilizers, chelating agents, preservatives, fragrances and the like may be blended, as appropriate in accordance with need.

In the sunscreen cosmetic of the present invention, even without blending in a volatile cyclic silicone, such as cyclopentasiloxane, which is normally blended into water-in-oil emulsion cosmetics in order to provide a good touch in use, a sunscreen cosmetic that is not sticky, that has a good feeling in use and that has increased ultraviolet protection power can be obtained. Thus, the cosmetic of the present invention includes modes in which a cyclic silicone is not blended.

The sunscreen cosmetic of the present invention can be prepared in a format such as a milky lotion, a cream, a lotion, a spray or the like, and can be manufactured by using conventional methods suitable for each format.

EXAMPLES

Although the present invention will be explained in further detail by providing examples below, the present invention is not limited in any way thereby. Where not otherwise noted, the blended amounts represent the percentages by mass of those components relative to the systems in which they are blended. Before specifically explaining each example, the evaluation methods that were employed will be explained.

1. Texture

Samples of the examples and comparative examples were actually used by ten expert panelists and evaluated regarding texture (lack of stickiness, wateriness). A five-level organoleptic evaluation was performed by each panelist in accordance with the evaluation scoring criteria below, and assessments were made based on the below-mentioned evaluation criteria in accordance with the total points scored.

Evaluation Scoring Criteria
   5: Very good
   4: Good
   3: Normal
   2: Poor
   1: Very poor Evaluation Criteria
   A: 40 or more total points
   B: 30 to 39 total points
   C: 29 or fewer total points 2. Measurement of Ultraviolet Protection Power Increase Rate Cosmetics (samples) according to each example were dripped, at a rate of 2 mg/cm$^2$, onto measurement plates (S plates) (5×5 cm V-groove PMMA plates, SPFMASTER-PA01), applied by finger for 60 seconds, and dried for 15 minutes to form coating films, the absorbances of which were measured using a Hitachi U-3500 self-recording spectrophotometer. The absorbances (Abs) were computed, with an uncoated plate as the control, by using the following equation, and the measurement values were integrated from 280 nm to 400 nm to determine the absorbance integral value.

$$Abs = -\log(T/To)$$

T: transmittance of sample, To: transmittance of uncoated plate

From the absorbance integral values of the samples that were determined, the ultraviolet protection power increase rates, relative to a sample (reference sample) in which a water phase thickener and a medicinal agent were not blended, were computed from the following equation.

[Ultraviolet protection power increase rate (%)]= [Absorbance integral value of sample]/[Absorbance integral value of reference sample]×100

Examples 1 to 10, Comparative Examples 1 to 6 and Reference Sample

Water-in-oil emulsion cosmetics having the compositions described in Table 1 and Table 2 below were prepared. The textures and the ultraviolet protection power increase rates were evaluated in accordance with the above-mentioned evaluation method.

TABLE 1

|  | Ex. 1 | Ex. 2 | Ex. 3 | Ex. 4 | Ex. 5 | Ex. 6 | Comp. Ex. 1 |
|---|---|---|---|---|---|---|---|
| Water | bal | bal | bal | bal | bal | bal | bal |
| Sodium polyacrylate | 0.1 | — | — | — | — | — | — |
| (Acrylates/(C10-30) alkyl acrylate) crosspolymer | — | 0.1 | — | — | — | — | — |
| Carboxy vinyl polymer | — | — | 0.1 | — | — | — | — |
| (PEG-240/decyl tetradeceth-20/HDI) copolymer | — | — | — | 0.1 | — | — | — |
| (Dimethylacrylamide/sodium acryloyldimethyl taurate) crosspolymer | — | — | — | — | 0.1 | — | — |
| (Acrylates/steareth-20 methacrylate) copolymer 30% aqueous solution | — | — | — | — | — | 0.1 | — |
| Stearoxyhydroxypropyl methylcellulose | — | — | — | — | — | — | 0.1 |
| Cellulose nanofiber | — | — | — | — | — | — | — |
| Agar | — | — | — | — | — | — | — |
| Xanthan gum | — | — | — | — | — | — | — |
| 2-Amino-2-methyl-1,3-propanediol | 1 | 1 | 1 | 1 | 1 | 1 | 1 |
| Tranexamic acid | 2 | 2 | 2 | 2 | 2 | 2 | 2 |
| EDTA•3Na—2H2O | 0.2 | 0.2 | 0.2 | 0.2 | 0.2 | 0.2 | 0.2 |
| Ethanol | 5 | 5 | 5 | 5 | 5 | 5 | 5 |
| 1,3-Butylene glycol | 2 | 2 | 2 | 2 | 2 | 2 | 2 |
| Glycerin | 3 | 3 | 3 | 3 | 3 | 3 | 3 |
| Phenoxyethanol | 0.5 | 0.5 | 0.5 | 0.5 | 0.5 | 0.5 | 0.5 |
| Isododecane | 20 | 20 | 20 | 20 | 20 | 20 | 20 |
| Diisopropyl sebacate | 6 | 6 | 6 | 6 | 6 | 6 | 6 |
| Isostearic acid | 0.1 | 0.1 | 0.1 | 0.1 | 0.1 | 0.1 | 0.1 |
| Sorbitan sesquiisostearate | 1 | 1 | 1 | 1 | 1 | 1 | 1 |
| PEG-9 polydimethylpolysiloxyethyl dimethicone | 4 | 4 | 4 | 4 | 4 | 4 | 4 |
| Dimethyldistearylammonium hectorite | 0.2 | 0.2 | 0.2 | 0.2 | 0.2 | 0.2 | 0.2 |
| Fatty acid-treated zinc oxide | 14 | 14 | 14 | 14 | 14 | 14 | 14 |
| Methyl methacrylate crosspolymer | 3 | 3 | 3 | 3 | 3 | 3 | 3 |
| Ethylhexyl methoxycinnamate | 7 | 7 | 7 | 7 | 7 | 7 | 7 |
| Phenylbenzimidazole sulfonic acid | 1 | 1 | 1 | 1 | 1 | 1 | 1 |
| Bis-ethylhexyloxyphenol methoxyphenyl triazine | 0.5 | 0.5 | 0.5 | 0.5 | 0.5 | 0.5 | 0.5 |
| Diethylamino hydroxybenzoyl hexyl benzoate | 1.5 | 1.5 | 1.5 | 1.5 | 1.5 | 1.5 | 1.5 |
| Evaluation 1. Texture | A | A | A | A | B | A | B |
| 2. Ultraviolet protection power increase rate | 111.1 | 111 | 109.4 | 107.1 | 107 | 105.4 | 98.8 |

TABLE 1-continued

| | Comp. Ex. 2 | Comp. Ex. 3 | Comp. Ex. 4 | Comp. Ex. 5 | Ref. Sample |
|---|---|---|---|---|---|
| Water | bal | bal | bal | bal | bal |
| Sodium polyacrylate | — | — | — | — | — |
| (Acrylates/(C10-30) alkyl acrylate) crosspolymer | — | — | — | — | — |
| Carboxy vinyl polymer | — | — | — | — | — |
| (PEG-240/decyl tetradeceth-20/HDI) copolymer | — | — | — | — | — |
| (Dimethylacrylamide/sodium acryloyldimethyl taurate) crosspolymer | — | — | — | — | — |
| (Acrylates/steareth-20 methacrylate) copolymer 30% aqueous solution | — | — | — | — | — |
| Stearoxyhydroxypropyl methylcellulose | — | — | — | — | — |
| Cellulose nanofiber | 1 | — | — | — | — |
| Agar | — | 0.1 | — | — | — |
| Xanthan gum | — | — | 0.1 | — | — |
| 2-Amino-2-methyl-1,3-propanediol | 1 | 1 | 1 | 1 | 1 |
| Tranexamic acid | 2 | 2 | 2 | 2 | — |
| EDTA•3Na—2H2O | 0.2 | 0.2 | 0.2 | 0.2 | 0.2 |
| Ethanol | 5 | 5 | 5 | 5 | 5 |
| 1,3-Butylene glycol | 2 | 2 | 2 | 2 | 2 |
| Glycerin | 3 | 3 | 3 | 3 | 3 |
| Phenoxyethanol | 0.5 | 0.5 | 0.5 | 0.5 | 0.5 |
| Isododecane | 20 | 20 | 20 | 20 | 20 |
| Diisopropyl sebacate | 6 | 6 | 6 | 6 | 6 |
| Isostearic acid | 0.1 | 0.1 | 0.1 | 0.1 | 0.1 |
| Sorbitan sesquiisostearate | 1 | 1 | 1 | 1 | 1 |
| PEG-9 polydimethylpolysiloxyethyl dimethicone | 4 | 4 | 4 | 4 | 4 |
| Dimethyldistearylammonium hectorite | 0.2 | 0.2 | 0.2 | 0.2 | 0.2 |
| Fatty acid-treated zinc oxide | 14 | 14 | 14 | 14 | 14 |
| Methyl methacrylate crosspolymer | 3 | 3 | 3 | 3 | 3 |
| Ethylhexyl methoxycinnamate | 7 | 7 | 7 | 7 | 7 |
| Phenylbenzimidazole sulfonic acid | 1 | 1 | 1 | 1 | 1 |
| Bis-ethylhexyloxyphenol methoxyphenyl triazine | 0.5 | 0.5 | 0.5 | 0.5 | 0.5 |
| Diethylamino hydroxybenzoyl hexyl benzoate | 1.5 | 1.5 | 1.5 | 1.5 | 1.5 |
| Evaluation  1. Texture | B | B | B | B | B |
| 2. Ultraviolet protection power increase rate | 98 | 97 | 93.2 | 101.1 | 100 |

As indicated in Table 1, compared with the Reference Sample in which the thickener and the medicinal agent of the present invention were not blended, an increase in the ultraviolet protection power was observed in the cosmetic of Comparative Example 5, in which only the medicinal agent (tranexamic acid) of the present invention was blended. In the cosmetics of Examples 1 to 6, in which thickeners of the type in the present invention were blended in addition to the medicinal agent of the present invention, the ultraviolet protection power increase rate further increased. Although the cosmetic of Example 5, in which (dimethylacrylamide/sodium acryloyldimethyl taurate) crosspolymer was added as the thickener, had a slightly inferior texture, the cosmetics of Examples 1-4 and 6 also had an excellent touch in use.

In contrast therewith, in the cosmetics of Comparative Examples 1 to 4, in which water-soluble thickeners derived from sugars were blended, not only was an increase in the ultraviolet protection power not observed, but also, the touch in use was also inferior.

TABLE 2

| | Ex. 7 | Ex. 8 | Ex. 9 | Ex. 10 | Comp. Ex. 6 | Ref. Sample |
|---|---|---|---|---|---|---|
| Water | bal | bal | bal | bal | bal | bal |
| Sodium polyacrylate | 0.1 | 0.1 | 0.1 | 0.1 | 0.1 | — |
| 2-Amino-2-methyl-1,3-propanediol | 1 | 1 | 1 | 1 | 1 | 1 |
| Tranexamic acid | 2 | — | — | — | — | — |
| Potassium methoxysalicylate | — | 1 | — | — | — | — |
| Dipotassium glycyrrhizinate | — | — | 1 | — | — | — |
| Nicotinic acid amide | — | — | — | 1 | — | — |
| EDTA•3Na—2H2O | 0.2 | 0.2 | 0.2 | 0.2 | 0.2 | 0.2 |
| Ethanol | 5 | 5 | 5 | 5 | 5 | 5 |
| 1,3-Butylene glycol | 2 | 2 | 2 | 2 | 2 | 2 |
| Glycerin | 3 | 3 | 3 | 3 | 3 | 3 |
| Phenoxyethanol | 0.5 | 0.5 | 0.5 | 0.5 | 0.5 | 0.5 |
| Isododecane | 20 | 20 | 20 | 20 | 20 | 20 |
| Diisopropyl sebacate | 6 | 6 | 6 | 6 | 6 | 6 |
| Isostearic acid | 0.1 | 0.1 | 0.1 | 0.1 | 0.1 | 0.1 |
| Sorbitan sesquiisostearate | 1 | 1 | 1 | 1 | 1 | 1 |
| PEG-9 polydimethylpolysiloxyethyl dimethicone | 4 | 4 | 4 | 4 | 4 | 4 |
| Dimethyldistearylammonium hectorite | 0.2 | 0.2 | 0.2 | 0.2 | 0.2 | 0.2 |
| Fatty acid-treated zinc oxide | 14 | 14 | 14 | 14 | 14 | 14 |
| Methyl methacrylate crosspolymer | 3 | 3 | 3 | 3 | 3 | 3 |
| Ethylhexyl methoxycinnamate | 7 | 7 | 7 | 7 | 7 | 7 |

TABLE 2-continued

| | Ex. 7 | Ex. 8 | Ex. 9 | Ex. 10 | Comp. Ex. 6 | Ref. Sample |
|---|---|---|---|---|---|---|
| Phenylbenzimidazole sulfonic acid | 1 | 1 | 1 | 1 | 1 | 1 |
| Bis-ethylhexyloxyphenol methoxyphenyl triazine | 0.5 | 0.5 | 0.5 | 0.5 | 0.5 | 0.5 |
| Diethylamino hydroxybenzoyl hexyl benzoate | 1.5 | 1.5 | 1.5 | 1.5 | 1.5 | 1.5 |
| Evaluation     1. Texture | A | A | A | A | A | B |
| 2. Ultraviolet protection power increase rate | 111.1 | 108.3 | 107.6 | 110.5 | 102 | 100 |

As indicated in Table 2, a synergistic increase in the ultraviolet protection power was observed in the cosmetics of Examples 7 to 10, in which thickeners and medicinal agents of the type in the present invention were combined and blended, as compared with the Reference Sample, in which neither the medicinal agent nor the thickener of the present invention were blended, and the cosmetic of Comparative Example 6, in which only the thickener (sodium polyacrylate) of the present invention was blended. Additionally, this synergistic increase effect was particularly prominent in the cases in which medicinal agents that are not salts were blended (Example 7 and Example 10). Additionally, the cosmetics of Examples 7 to 10 were not sticky and also had an excellent touch in use.

Hereinafter, examples of formulations of the cosmetic of the present invention will be indicated. Needless to say, the present invention is not limited in any way by these formulation examples, and is as defined by the claims. The blended amounts are all indicated in percentage by mass relative to the entire cosmetic.

Formulation Example 1

Water-in-Oil Emulsion Sunscreen Cosmetic

| (Component name) | Blended amount (% by mass) |
|---|---|
| Water | balance |
| Sodium polyacrylate | 0.1 |
| 2-Amino-2-methyl-1,3-propanediol | 1 |
| Tranexamic acid | 2 |
| EDTA•3Na—2H$_2$O | 0.2 |
| Ethanol | 5 |
| 1,3-Butylene glycol | 2 |
| Glycerin | 3 |
| Phenoxyethanol | 0.5 |
| Isododecane | 20 |
| Diisopropyl sebacate | 6 |
| Isostearic acid | 0.1 |
| Sorbitan sesquiisostearate | 1 |
| PEG-9 polydimethylpolysiloxyethyl dimethicone | 4 |
| Dimethyldistearylammonium hectorite | 0.2 |
| Fatty acid-treated zinc oxide | 14 |
| Corn starch | 3 |
| Ethylhexyl methoxycinnamate | 7 |
| Phenylbenzimidazole sulfonic acid | 1 |
| Bis-ethylhexyloxyphenol methoxyphenyl triazine | 0.5 |
| Diethylamino hydroxybenzoyl hexyl benzoate | 1.5 |

Formulation Example 2

Water-in-Oil Emulsion Sunscreen Cosmetic

| (Component name) | Blended amount (% by mass) |
|---|---|
| Water | balance |
| Sodium polyacrylate | 0.1 |
| 2-Amino-2-methyl-1,3-propanediol | 1 |
| Tranexamic acid | 2 |
| EDTA•3Na—2H$_2$O | 0.2 |
| Ethanol | 5 |
| 1,3-Butylene glycol | 2 |
| Glycerin | 3 |
| Phenoxyethanol | 0.5 |
| Isododecane | 20 |
| Diisopropyl sebacate | 6 |
| Isostearic acid | 0.1 |
| Sorbitan sesquiisostearate | 1 |
| PEG-9 polydimethylpolysiloxyethyl dimethicone | 4 |
| Dimethyldistearylammonium hectorite | 0.2 |
| Fatty acid-treated zinc oxide | 14 |
| Silica | 3 |
| Ethylhexyl methoxycinnamate | 7 |
| Phenylbenzimidazole sulfonic acid | 1 |
| Bis-ethylhexyloxyphenol methoxyphenyl triazine | 0.5 |
| Diethylamino hydroxybenzoyl hexyl benzoate | 1.5 |

The invention claimed is:

1. A water-in-oil emulsion sunscreen cosmetic comprising:

(A) an ultraviolet absorbing agent;

(B) a medicinal agent selected from the group consisting of L-ascorbic acid and derivatives thereof, tranexamic acid and derivatives thereof, alkoxysalicylic acid and derivatives thereof, glycyrrhizinic acid and glycyrrhizinic acid salts, and nicotinic acid and derivatives thereof;

(C) a water-soluble thickener that is not sugar-derived; and (D) water, wherein the (C) water-soluble thickener is a single type or a combination of two or more types selected from sodium polyacrylate, (acrylates/C10-30 alkyl acrylate) crosspolymer, carboxyvinyl polymer, (PEG-240/decyl tetradeceth-20/hexamethyl diisocyanate) copolymer, (dimethylacrylamide/sodium acryloyldimethyl taurate) crosspolymer, and (acrylates/steareth-20 methacrylate) copolymer.

2. The cosmetic as in claim 1, wherein the component (C) is one or more substances selected from among vinyl-based polymers, acrylic-based polymers, acrylate-based synthetic polymers and hydrophobically modified polyether urethanes.

3. The cosmetic as in claim 1, wherein a blended amount of the component (D) is 13% to 80% by mass relative to the entire cosmetic.

4. The cosmetic as in claim 1, wherein the medicinal agent is not a salt.

\* \* \* \* \*